United States Patent [19]

Messinger

[11] Patent Number: 5,076,660
[45] Date of Patent: Dec. 31, 1991

[54] LIGHT SOURCE RECEPTACLE FOR FIBEROPTIC ILLUMINATION

[75] Inventor: Elmar K. Messinger, Huntington Station, N.Y.

[73] Assignee: Olympus Corporation, Lake Success, N.Y.

[21] Appl. No.: 470,738

[22] Filed: Jan. 26, 1990

[51] Int. Cl.$^5$ .......................................... G02B 23/26
[52] U.S. Cl. ..................................... 385/119; 128/23; 385/31
[58] Field of Search .......................... 350/96.26, 96.29; 128/4, 6, 423; 604/892.45

[56] References Cited

U.S. PATENT DOCUMENTS

| | | | |
|---|---|---|---|
| 3,299,884 | 1/1967 | Moore et al. | 128/23 |
| 3,499,107 | 3/1970 | Sheldon | 350/96.26 X |
| 4,572,609 | 2/1986 | Sakuragi et al. | 350/96.29 X |
| 4,898,172 | 2/1990 | Grable | 128/28 X |

Primary Examiner—William L. Sikes
Assistant Examiner—Phan T. Heartney
Attorney, Agent, or Firm—Kenyon & Kenyon

[57] ABSTRACT

A fiberoptic bundle or liquid light guide for a borescope, fiberscope or videoscope is coupled to the light source using a light guide coupler having a plurality of air passages to vent excess heat. The illumination unit comprises a fan that draws cool air through the passages into the light source to remove excess heat from the light guide coupler. Heat radiators can be added to the coupler to increase its surface area and to improve heat dissipation. Air baffles can be added to optimize the air flow through the light guide coupler. The light guide coupler thus acts as a heat sink while dissipating excess heat using an air flow caused by the difference in air pressure created by the fan in the illumination unit.

12 Claims, 2 Drawing Sheets

LIGHT SOURCE RECEPTACLE FOR FIBEROPTIC ILLUMINATION

BACKGROUND OF THE INVENTION

The present invention relates to a receptacle for launching light into a light guide formed from, for example, a fiberoptic bundle or a tube filled with a liquid.

There are presently two types of instruments used to visually inspect internal surfaces in objects which an inspector cannot see without disassembling or cutting apart the object, the fiberscope and the videoscope. Both these instruments are flexible. The fiberscope employs a coherent fiberoptic image bundle to relay an image from an objective lens at a distal tip of the instrument back to the eyepiece. The videoscope differs in having a miniature CCD chip television camera at its tip to relay the image. Another instrument is the borescope which is a rigid instrument with a series of lenses similar to a telescope. The present invention applies to all three of these instruments.

These instruments use a light guide to transmit light from an external light source unit through the instrument to illuminate the internal area to be inspected. These external light source units can use a variety of lamps such as an incandescent tungsten filament bulb or a gas discharge lamp as the source of light. These light sources also generate tremendous amounts of heat in the form of infrared radiant energy. The lamp reflector focuses the heat as well as the light onto the metal tip area of the light guide plug and the receptacle holding it. The temperature can become excessive and cause the epoxy binding the glass fibers to burn, melt and discolor, and thus destroy the light transmission of the light guide. Moreover, serious burns to the fingers can result if the operator does not follow instructions, ignores safety cautions and handles the tip of a light guide just after removing it from the light source. The build-up of heat on the tip is often sufficient to cause serious burns on the fingers. The hot light guide tip can also present a fire hazard if mistakenly placed on flammable material.

The trend in the industry is toward using video displays with smaller diameter instruments in which the light guides carry more light. This trend requires higher intensity light sources such as metal halide gas discharge lamps or xenon gas discharge lamps for visible light and mercury gas discharge lamps for ultraviolet illumination. All of these lamps produce enormous amounts of heat. These higher intensity light sources can make the metal tip of light guides and the metal receptacle much more prone to reach excessive temperatures.

SUMMARY OF THE INVENTION

The present invention relates to a coupler or receptacle for connecting a light guide to a light source unit in which the coupler has a plurality of air passages to vent excess heat. The light source unit comprises a fan arranged to draw cool air through the passages to remove heat from the coupler. Heat radiators in the form of baffles can be added to the coupler to increase its surface area and to improve heat dissipation. Additional air baffles in the light source unit can be added to control the air flow around and through the coupler. The coupler of the present invention thus acts as a heat sink by dissipating heat from the coupler using an air flow caused by the differences in air pressure created by the fan.

Experiment has shown that the maximum cooling can be obtained by creating a low pressure behind the coupler on the side facing the light source unit. Cool air from outside the coupler then flows into the light source unit through the coupler. Alternately, cool air could be blown into the light source unit and directly out the air channels of the coupler to remove heat from the coupler.

Air baffles can be used to control the air flow in the channels of the light guide coupler so as to maximize the dissipation of heat.

The light source unit can further comprise a spring loaded safety shutter to prevent someone from accidentally looking into the lamp and damaging his or her eye. The shutter can be coated with a reflective material to reflect light back to the light source and thus minimize the amount of radiant energy which it must absorb. The light source unit can also include a shutter that is activated by a switch and that closes whenever the light source is not in use even when a light guide is connected to the coupler. This "dead man" switch helps prevent the surface of the target from absorbing excess heat from the high intensity light. This feature is through to have utility when using the high intensity light source unit in an environment containing flammable materials.

A further feature of the present invention arranges a plurality of focusing lenses on a wheel to focus the light from the light source into different illumination areas. The lens wheel permits maximizing the efficiency of the light transfer into, for example, fiberoptic bundles or liquid light guides that have different diameters by matching the illumination area to the diameter of the light guide. The aim is to fully illuminate all of the light guide without spilling light onto the adjacent light guide coupler where it only heats the light guide coupler without illuminating the target.

DETAILED DESCRIPTION

Figure 1:
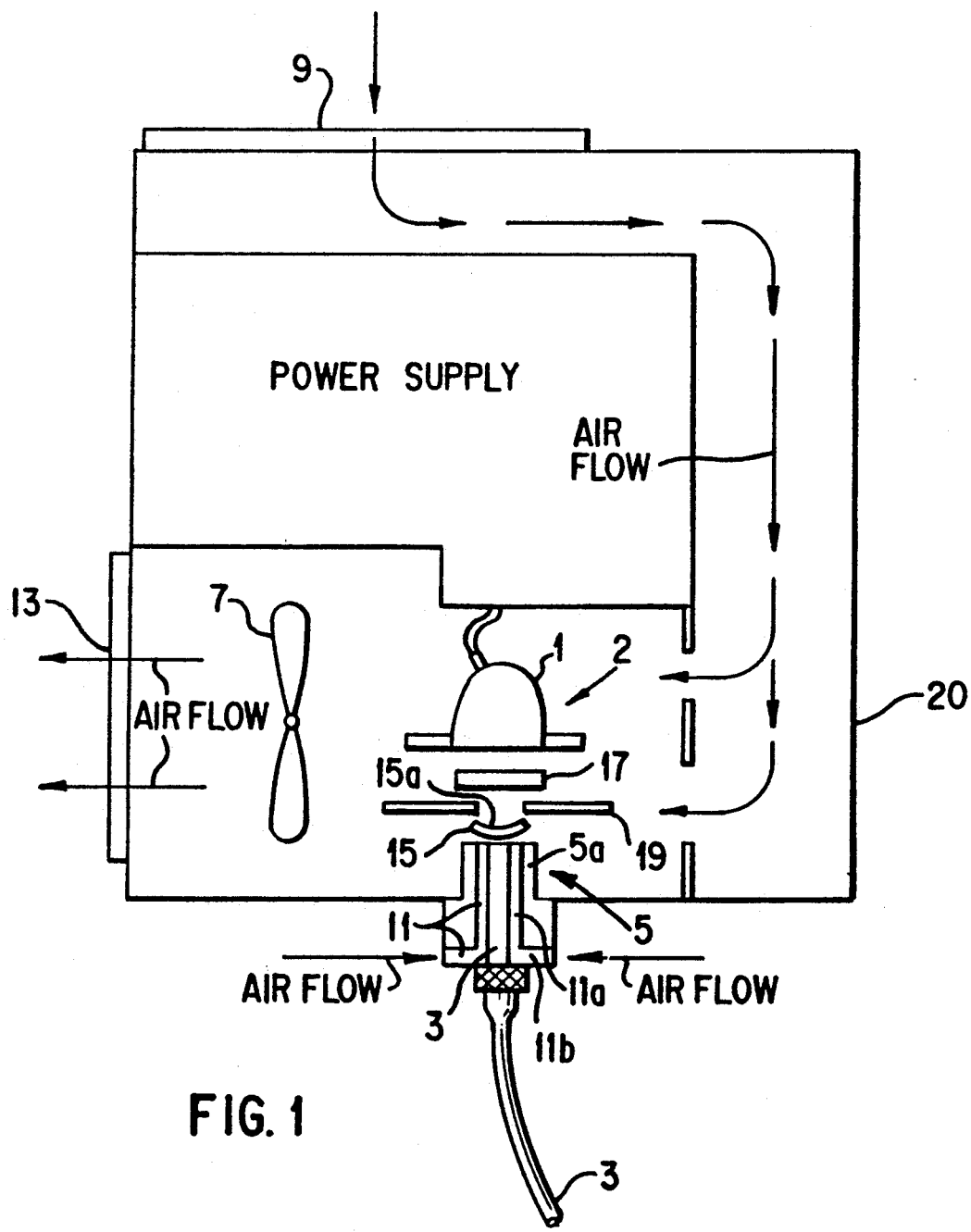
FIG. 1 shows a light source and air cooled light guide receptacle according to the present invention.

Referring to FIG. 1, a lamp 1 launches light into a light guide 3. The light guide may comprise, for example, a fiberoptic bundle or a tube filled with an appropriate liquid. The light guide coupler 5 supports the light guide plug 3 on the surface of light source unit 2. A fan 7 circulates air around lamp 1 and the light guide coupler 5. Fan 7 preferably draws cool air through air intake 9 and cooling passages 11 before expelling it through exit aperture 13. An air foil shutter 15 and lens arrangement 17 are positioned on opposite sides of a heat baffle 19. Shutter 15 has the air foil shape shown in FIG. 1 so as to create half of a Venturi nozzle at the end of coupler 5. The low pressure in the throat of the nozzle increased the difference in air pressure between the light source 1 and the outside air so as to maximize the amount of cool air drawn through the light guide coupler 2.

Figure 2:
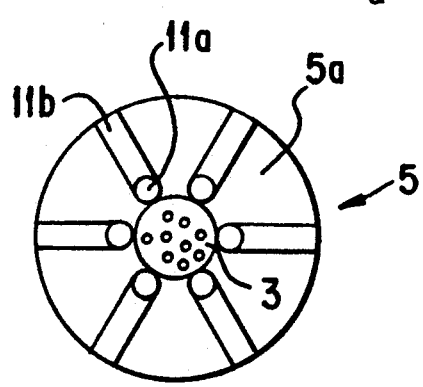
FIG. 2 shows a cross-section of the light guide coupler shown in FIG. 1.

FIG. 2 shows a cross-section of the light guide coupler shown in FIG. 1. The air passages 11 are shown divided into two components, passages 11a and 11b, corresponding to the vertical and horizontal air passage, respectively. The inner air passages 11a are bounded by the outer surface of the light guide plug 3 as shown in FIG. 2. Alternately, however, the air passages could be enclosed entirely within the light guide coupler 5.

Figure 3:
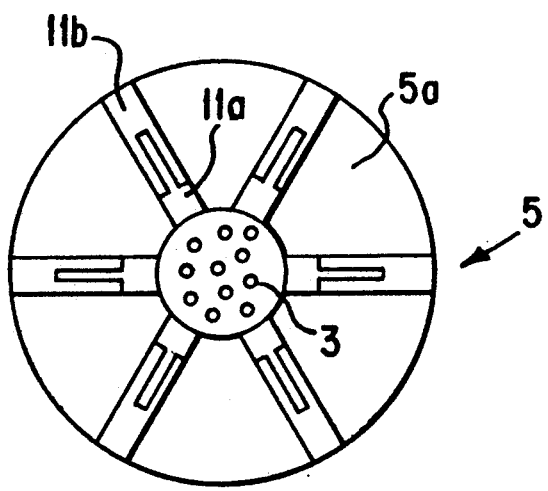
FIG. 3 shows an alternate embodiment of the light guide coupler shown in FIG. 2 having wider air channels to increase the dissipation of heat from the light guide coupler.

FIG. 3 shows an alternate embodiment of the light guide coupler shown in FIG. 2. The channels 11a are shown as elongated air baffles that present a greater surface area to the cool air stream. The elongated shape should transfer heat away from the fiberoptic coupler 5 more efficiently. It is to be appreciated that the maximum heat dissipation in the fiberoptic couplers shown in either FIGS. 2 or 3 occurs along lower passages 11b because they receive the coolest air. This result is desirable because it reduces the temperature of the coupler most in the region most apt to be touched by the user. Alternately, the air passages could be formed as direct passages through the coupler so that the air flow is not obstructed by the right angle turn between passages 11a and 11b. The direct passages could provide better air circulation.

Figure 4:
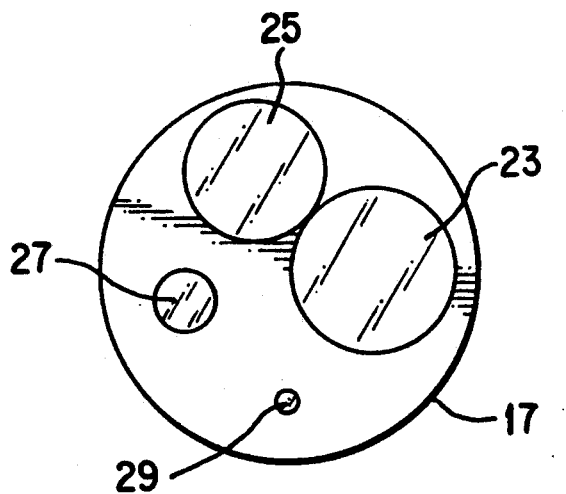
FIG. 4 shows a lens wheel of the type used in FIG. 1 to focus the light onto the light guide.

FIG. 4 is an enlargement of the lens wheel 17 shown in FIG. 1. A plurality of lenses 23-29 are shown distributed around the circumference of wheel 17. Each lens focuses the light from lamp 1 at the input to the light guide 3. Each lens, however, forms an illumination area having a different diameter. The lens wheel 17 thus allows connecting light guides that have different sizes. Each lens should fully illuminate the diameter of the entire bundle so that the output is also fully illuminated. However, the diameter of the illumination is ideally well defined so that no excess light spills onto the light guide coupler 5 since any spill light will only heat the light guide coupler 5.

The light guide coupler of the present invention permits the light source shown in FIG. 1 to supply light to the light guide coupler whenever shutter 15 is open. Shutter 15 is spring loaded so that it opens when the light guide plug 3 is inserted completely into the light guide coupler 5 and allows light to shine upon the tip of the light guide 3. When the light guide 3 is removed from the coupler, the shutter closes which prevents light from shining out of the center of the coupler 5. This safety feature protects the eyes by preventing anyone from looking directly into the lamp.

A switch, not shown, controls the actuation of both lamp 1 and fan 7. It is preferred that fan 7 continue operating for a brief period of time after lamp 1 turns off so as to vent any excess heat build up during operation.

The present invention allows an ALS 6250 high intensity light source to operate at full brightness for more than 200 hours nonstop. The temperature of the light source coupler 5 as measured did not exceed 75° C. (168° F.). Moreover, the coupler was cool enough to touch after only a few minutes of cooling with the fan on. The present invention thus permits different light guides to be connected to the same light source unit with little delay and to quickly handle equipment for packing in its storage case within minutes of completing its use.

The principles, preferred embodiments and models of operation of the present invention have been described in foregoing specification. The invention which is intended to be protected herein should not, however, be construed as limited to the teachings of the specification because they merely illustrate the invention. There should be other ways to practice the present invention that will come within the meets and bounds of the inventions identified in the following claims as well as within the penumbra of the invention they define.

What is claimed is:

1. A light source for a fiber optic borescope, a fiberscope or a videoscope comprising:
   a) a housing having a wall;
   b) a lightguide;
   c) a lightguide coupler comprising:
      i) a plug mounted on the end of the lightguide arranged so the end of the lightguide is exposed to receive light;
      ii) a receptacle mounted in said wall including a body defining a bore into which the plug is inserted with said end of said lightguide exposed, said body having a wall surrounding said bore; and
      iii) a plurality of passages formed in said coupler surrounding said lightguide;
   d) a lamp;
   e) a lens focusing light from said lamp on the end of said lightguide; and
   f) means for moving air through said passages, whereby air can be drawn through said passages in either direction to cool said coupler and said lightguide.

2. Apparatus according to claim 1 wherein said passages are formed in the wall of said receptacle.

3. Apparatus according to claim 1 wherein said means for moving air comprises a fan within said housing.

4. Apparatus according to claim 3 wherein said housing further includes:
   a) an air inlet;
   b) an air outlet; and wherein
   c) said fan is disposed to draw air in from said inlet and past said light source and coupler to said outlet whereby air will also be drawn into or expelled from said housing through said passages from the outside.

5. Apparatus according to claim 4 and further including baffles disposed to increase the air flow speed past said coupler so as to increase the amount of air flowing through said passages.

6. Apparatus according to claim 4 and further comprising a shutter for selectively blocking light from the lamp from reaching the lightguide coupler.

7. Apparatus according to claim 6, wherein said shutter has a surface facing the lamp and a reflective material deposited on the surface.

8. Apparatus according to claim 7, wherein the reflective material is chosen from the group consisting of aluminum and silver.

9. Apparatus according to claim 1 wherein said lens is one of a plurality of lenses distributed on a rotating wheel, the lenses of said plurality being selectively positionable between the lamp and the lightguide coupler whereby light can be focused on different sizes of lightguides.

10. A method of cooling a lightguide coupler in a light source for a fiber optic borescope, a fiberscope or a videoscope which comprises:
   a) a housing having a wall;
   b) a lightguide;

c) a lightguide coupler comprising:
  i) a plug mounted on the end of the lightguide arranged so the end of the lightguide is exposed to receive light; and
  ii) a receptacle mounted in said wall including a body defining a bore into which the plug is inserted with said end of said lightguide exposed, said body having a wall surrounding said bore;
d) a lamp; and
e) a lens focusing light from said lamp on the end of said lightguide, comprising the steps of:

i) forming a plurality of passages in said lightguide coupler; and
  ii) drawing air through said plurality of air passages.

11. A method as claimed in claim 10, wherein the step of drawing the air through the lightguide coupler comprises the steps of:
  a) drawing cool air from outside the housing into the housing through said passages; and
  b) discharging warm air from the housing.

12. The method according to claim 11 wherein said step of drawing cool air comprises drawing cool air from outside the housing into the housing.

* * * * *

UNITED STATES PATENT AND TRADEMARK OFFICE
CERTIFICATE OF CORRECTION

PATENT NO. : 5,076,660
DATED : December 31, 1991
INVENTOR(S) : Elmar K. Messinger It is certified that error appears in the above-identified patent and that said Letters Patent is hereby corrected as shown below:

<u>Column</u>  <u>Line</u>
2         25        Change "through" to --thought--.

Signed and Sealed this

Thirteenth Day of July, 1993

*Attest:*

MICHAEL K. KIRK

*Attesting Officer*  Acting Commissioner of Patents and Trademarks